United States Patent [19]

Cook et al.

[11] Patent Number: 5,446,215
[45] Date of Patent: Aug. 29, 1995

[54] PRODUCTION OF HYDROFLUOROCARBONS

[75] Inventors: Malcolm R. Cook, Chester; John D. Scott, Cheshire, both of United Kingdom

[73] Assignee: Imperial Chemical Industries PLC, London, England

[21] Appl. No.: 70,950

[22] Filed: Jun. 4, 1993

[30] Foreign Application Priority Data

Jun. 11, 1992 [GB] United Kingdom ............... 9212410

[51] Int. Cl.$^6$ ............................................ C07C 21/18
[52] U.S. Cl. ..................................................... 570/142
[58] Field of Search ........................................ 570/142

[56] References Cited

U.S. PATENT DOCUMENTS 3,377,394  4/1968  Boudakian et al. .
5,344,998  9/1994  Martin et al. ................. 570/142
5,386,064  1/1995  Woodcock et al. .............. 570/142

FOREIGN PATENT DOCUMENTS

0518506A2  12/1992  European Pat. Off. .

OTHER PUBLICATIONS

Knunyants et al., "Some Reactions of Fluorine-Containing Ethers", Bulletin of the Academy of Sciences of the USSR, Div of Chemical Science, Oct. 1972, vol. 21, No. 10, pp. 2177–2180.

*Primary Examiner*—Alan Siegel
*Attorney, Agent, or Firm*—Cushman Darby & Cushman

[57] ABSTRACT

A process for the production of a hydro(halo)fluorocarbon which comprises contacting an $\alpha$-fluoroether in the vapour phase at an elevated temperature with a catalyst and wherein the catalyst is treated whereby to maintain and/or restore its activity.

The catalyst treatment comprises either: (i) heating the catalyst to an elevated temperature above about 250° C. in the absence of an $\alpha$-fluoro ether, or (ii) contacting the catalyst at an elevated temperature with an oxidising agent whilst or between the times when the $\alpha$-fluoro ether is contacted with the catalyst. The catalyst may be an oxidation promoting metal, for example zinc, iron or copper, carried on a metal oxide, fluoride or oxyfluoride support.

7 Claims, No Drawings

PRODUCTION OF HYDROFLUOROCARBONS

This invention relates to a process for the production of hydrofluorocarbons, in particular hydrofluoroalkanes such as difluoromethane by the catalysed thermal decomposition of α-fluoroethers in particular α-fluorodialkylethers such as bis(fluoromethyl)ether.

In recent years chlorofluorocarbons, which are used on a large scale around the world, have been perceived as having an adverse effect on the ozone layer and/or as contributing to global warming. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned environmentally harmful effects. One approach in the search for suitable replacements has centred on fluorocarbons which do not contain chlorine but which may contain hydrogen. The hydrofluorocarbon difluoromethane, also known as HFA 32, is of interest as one such replacement, in particular as a replacement in refrigeration, air-conditioning and other applications.

Several methods for the production of difluoromethane are known but many of these methods involve the use of chlorine-containing starting materials and the production of chlorine-containing by-products. Chlorine-free processes are also known and one one of these, the reaction between formaldehyde and hydrogen fluoride at an elevated temperature in the presence of a fluorine-containing inorganic acid, a metal fluoride, a metal oxide or a metal chromite, has been described in U.S. Pat. No. 3,377,394. The highest yield of difluoromethane reported from this reaction is 4.2%, the major product being methyl fluoride.

In our published European Patent Application No. 0 518 506, there is described a process for the production of difluoromethane by contacting bis(fluoromethyl)ether with a catalyst at elevated temperature in the vapour phase. This catalysed thermal decomposition of bis(fluoromethyl)ether may achieve high conversions, for example greater than 95% conversion, based on bis(fluoromethyl)ether with high yields, as high as 75%, or even 90% of difluoromethane, the other major product being monofluoromethane.

In our co-pending International Application No. PCT/GB92/02244 there is described a process for the production of hydrofluorocarbons by contacting an α-fluoroether other than bis(fluoromethyl)ether with a catalyst at elevated temperature in the vapour phase.

However, we have found that a drawback with the aforementioned processes of EP 0 518 506 and PCT/GB92/02244 is that the catalyst tends to become deactivated, the conversion of α-fluoroether, especially bis(fluoromethyl)ether falling significantly after what may be comparatively short periods of operation. Deactivation of the catalyst is due, we believe, to the formation of a carbonaceous overlay on the surface of the catalyst.

We have now found that the activity of the catalyst, that is the α-fluoroether conversion, may be maintained at, and/or restored to a high level by continually or periodically treating the catalyst, whilst, or between the times when the α-fluoroether is contacted with the catalyst.

According to the present invention there is provided a process for the production of a hydro(halo)fluorocarbon which comprises contacting an α-fluoroether in the vapour phase at an elevated temperature with a catalyst and wherein the catalyst is treated whereby to maintain and/or restore its activity.

By an α-fluoroether there is meant a fluorine-containing ether having a fluorine atom attached to a carbon atom in the α-position relative to the oxygen atom, that is an ether containing the group -C-O-CF- and thus an ether having the general formula $R-O-CFR^1R^2$, wherein R, $R^1$ and $R^2$ are as hereinafter defined.

We have found that α-fluoroethers of formula $R-O-CF-R^1R^2$ may be caused to breakdown upon heating to yield a hydro(halo)fluorocarbon R-F and a compound containing a carbonyl group, usually an aldehyde $R^1R^2CO$. The ether apparently breaks down by transference of an α-fluorine atom from one α-carbon atom to the other α-carbon atom to yield a hydro(halo)-fluorocarbon R-F (referred to hereafter as the fluorine-exchange product). The ether may in some cases also break down by transference of an α-hydrogen atom so that a hydro(halo)fluorocarbon R-H (referred to hereafter as the hydrogen-exchange product) may also be produced. α-fluoro-ethers may therefore be utilised as useful starting materials for the production of hydro(halo)fluoroalkanes.

In the α-fluoroether $R-O-CF-R^1R^2$, the group R may generally take any form provided that it comprises at least one carbon atom, and the group R may for example be saturated or unsaturated, cyclic or acyclic. Furthermore, the group R may be aliphatic or aromatic and it may be a substituted group such as a halo-substituted group.

The process of the invention is useful in particular for the production of hydrofluoroalkanes from ethers in which the R group is an optionally substituted alkyl group which may comprise one, two or even more carbon atoms, say up to 6 or even more carbon atoms. The alkyl group R will usually be a straight chain alkyl group although it may also be a branched chain alkyl group. The group R may comprise only carbon and hydrogen although it may contain other atoms such as halogen atoms; usually the group R will be a fluorinated group.

The α-fluoroether will typically be an α-fluoroalkyl ether, that is an ether of formula $R-O-CF-R^1R^2$ wherein $R^1$ and $R^2$ each represents a hydrogen atom, fluorine atom or an optionally substituted alkyl group which may comprise one, two or even more carbon atoms, say up to 6 or even more carbon atoms. The alkyl groups $R^1$ and $R^2$ will usually be straight chain alkyl groups although they may also be branched chain alkyl groups. The groups $R^1$ and $R^2$ may comprise only carbon and hydrogen although they may be substituted alkyl groups; usually the groups $R^1$ and $R^2$ will be fluorinated groups. Typically at least one of $R^1$ and $R^2$ will be a hydrogen atom.

According to a preferred embodiment of the invention there is provided a process for the production of hydro(halo)fluoroalkanes which comprises contacting an α-fluoroether having the formula $R-O-CF-R^1R^2$ wherein R is an optionally substituted alkyl group comprising from 1 to 6 carbon atoms and $R^1$ and $R^2$ each is H, F or an optionally substituted alkyl group containing from 1 to 6 carbon atoms in the vapour phase at an elevated temperature with a catalyst and wherein the catalyst is treated whereby to maintain and/or restore its activity.

The α-fluoroether is preferably an α-fluoromethylether, R-O-CFH$_2$, or a tetrafluoroethylether R-O-CFH-CF$_3$, since these α-fluoroethers are readily prepared and on heating in the vapour phase to elevated temperature in the presence of a catalyst yield particularly useful hydrofluorocarbons.

The α-fluoromethylether may be, for example, FCH$_2$-O-CH$_3$ (fluoromethyl-methylether), FCH$_2$-O-CH$_2$CF$_2$H (1,1,-difluoroethyl-fluoromethyl ether), or FCH$_2$-O-CH$_2$CF$_3$ (1,1,1-trifluoroethyl-fluoromethylether), which when heated in the vapour phase to elevated temperature may give the following hydrofluoroalkanes respectively, CH$_3$F, CHF$_2$CH$_2$F and CF$_3$CH$_2$F. The tetrafluoroethylether may be, for example, CF$_3$CHF-O-CH$_2$CF$_3$ or CF$_3$CFH-O-CH$_3$ (which upon heating in the vapour phase-to elevated temperature may yield 1,1,1,2-tetrafluoroethane) or CF$_3$CFH-O-CFHCF$_3$ or CF$_3$CHF-O-CH$_2$F (which upon heating in the vapour phase to elevated temperature may yield CF$_3$CF$_2$H and/or CF$_3$CFH$_2$).

According to an embodiment of the invention there is provided a process for the production of 1,1,1,2-tetrafluoroethane comprising contacting an α-fluoroalkylether selected from the group consisting of FCH$_2$-O-CH$_2$CF$_3$, FCH$_2$-O-CHFCF$_3$, CF$_3$CHF-O-CH$_2$CF$_3$ and CF$_3$CFH-O-CH$_3$ in the vapour phase at an elevated temperature with a catalyst and wherein the catalyst is treated whereby to maintain and/or restore its activity.

According to another embodiment of the invention there is provided a process for the production of pentafluoroethane comprising contacting CF$_3$CFH-O-CFHCF$_3$ or CF$_3$CFH-O-CH$_2$F in the vapour phase at an elevated temperature with a catalyst and wherein the catalyst is treated whereby to maintain and/or restore its activity.

It is to be understood that the process of the invention may lead to a product comprising a mixture of hydro(-halo)fluoroalkanes from a single α-fluoroether. Thus, for example, where the α-fluoroether is CH$_2$F-O-CH$_2$CF$_3$ the product may be a mixture of CH$_3$CF$_3$ and CF$_3$CH$_2$F. Furthermore, desirable mixtures of hydrofluoroalkanes may be produced, as desired, by employing mixtures of α-fluoroethers. Thus, for example, where a mixture of CH$_2$F-O-CH$_2$F and CF$_3$CH$_2$-O-CH$_2$F is heated to elevated temperature, the product may comprise a mixture of CH$_2$F$_2$, CH$_3$F and CF$_3$CH$_2$F.

In an especially preferred embodiment of the invention, the α-fluoroether which is contacted with a catalyst at elevated temperature in the vapour phase is CH$_2$F-O-CH$_2$F, bis(fluoromethyl)ether.

The invention will be described hereafter with reference to bis(fluoromethyl)ether although it is to be understood that the invention is not so limited and any α-fluoroether, or mixture thereof may be employed in the catalytic thermal decomposition process of the present invention.

We have discovered that the activity of the catalyst measured in terms of bis(fluoromethyl)ether conversion under controlled conditions of temperature and pressure, may be maintained at a high level for significantly longer periods of time than where the catalyst is not so treated, where the catalyst treatment comprises either:

(i) heating the catalyst to an elevated temperature above about 250° C. in the absence of bis(fluoromethyl)ether, or (ii) contacting the catalyst at an elevated temperature with an oxidising agent.

The conditions under which the production of difluoromethane from bis(fluoromethyl)ether is effected are described in our Published European Application No. 0 518 506, the contents of which are incorporated herein by reference.

In particular, suitable conditions of temperature and pressure, the presence of hydrogen fluoride and suitable and preferred catalysts are described therein.

Thus, the temperature to which the bis(fluoromethyl)ether is heated to produce difluoromethane is such that the bis(fluoromethyl)ether is in the vapour phase and the temperature will usually therefore be at least 80° C., preferably at least 200° C. and more preferably at least 250° C. The temperature need be no higher than about 500° C., although higher temperatures, say up to about 700° C., may be used if desired.

Heating of the bis(fluoromethyl)ether to produce difluoromethane may be carried out in the presence of hydrogen fluoride vapour. The hydrogen fluoride may be used as a diluent or carrier gas with which the bis(fluoromethyl)ether may be introduced into the reaction zone or the hydrogen fluoride may be introduced into the reaction zone separately.

Suitable catalysts include for example, a metal, for example an s-block metal such as calcium, a p-block metal such as aluminium, tin or antimony, an f-block metal such as lanthanum or a d-block metal such as nickel, copper, iron, manganese, cobalt and chromium or alloys thereof; a metal oxide, for example chromia or alumina, a metal fluoride, for example, aluminium, manganese or chromium fluoride, or a metal oxyfluoride, for example an oxyfluoride of one of the aforementioned metals. The metal is preferably a d- or p- block metal, oxide, fluoride or oxyfluoride thereof, and more preferably chromium, aluminium, or a Group VIIIa metal.

We have found that difluoromethane may be produced with very high selectivity where the catalyst employed comprises (i) a metal selected from the group consisting of aluminium, chromium, copper, iron and nickel or an alloy or mixture of at least one of these metals, or (ii) an oxide, fluoride or oxyfluoride of at least one of the metals or alloys defined in (i).

Where alloys are employed, the alloys may also comprise other metals, for example molybdenum. Examples of preferred alloys include Hastelloy and stainless steel; stainless steel is especially preferred.

Furthermore we prefer that these alloys are treated prior to use, for example by heating to elevated temperature in the presence of air or oxygen, suitable temperature being in the range from about 300° C. to about 500° C. Alternatively or additionally, this catalyst pre-treatment may be carried out in the presence of hydrogen fluoride.

Preferred catalysts are chromia and iron oxide which are very robust catalysts although they may not, in the absence of an oxidising agent, promote as high a degree of selectivity to difluoromethane as other catalysts, for example alloys. Chromia and iron oxide may also be given a pre-treatment as above prior to use.

The catalyst may also comprise mixtures of metals, oxides, fluorides or oxyfluorides thereof, such as for example impregnated metal oxide or oxyfluorides, or simple mixtures. Thus, for example the catalyst may comprise chromia impregnated with iron, nickel or other metals or compounds thereof, for example oxides or halides thereof or the catalyst may comprise a mixture of chromia and other metal oxides, for example iron oxide.

The catalyst may be present in the form of a fixed or fluidised bed.

The particular temperature to which the bis(fluoromethyl)ether is heated to produce difluoromethane is dependant at least to some extent upon the catalyst employed. Typically the temperature need be no higher than about 450° C. where a catalyst is used in the presence of hydrogen fluoride. Thus, for example, where the heating is effected in the presence of stainless steel and hydrogen fluoride, the temperature is preferably at least about 250° C. and more preferably at least 300° C. but need be no higher than about 400° C., generally no higher than about 350° C. However, where the catalyst is chromia in the presence of hydrogen fluoride, the temperature is preferably from about 180° C. to about 320° C., more preferably from about 200° C. to about 280° C.

The contacting of bis(fluoromethyl)ether with the catalyst to produce difluoromethane is conveniently carried out at about ambient pressure although superatmospheric or subatmospheric pressures may be used if desired. Indeed superatmospheric pressures up to about 15 bar at lower temperatures may be generally preferred since the yield of and selectivity to difluoromethane may be increased under such conditions.

Where the catalyst is treated by heating to a temperature above 250° C., the treatment is in the manner of a regeneration, that is the flow of bis(fluoromethyl)ether over the catalyst is temporarily switched off and the catalyst is regenerated or reactivated by heating the catalyst to a temperature above 250° C., and preferably at least about 300° C. This treatment may be performed in the presence of a diluent gas, for example nitrogen or hydrogen fluoride.

The preferred treatment comprises contacting the catalyst with an oxidising agent at an elevated temperature. This preferred treatment may be conducted in the manner of a regeneration or re-activation, that is the bis(fluoromethyl)ether flow over the catalyst may be temporarily switched off and the catalyst may be contacted with the oxidising agent so that the process may be operated by sequentially contacting the catalyst with bis(fluoromethyl)ether and then with an oxidising agent. The frequency with which the catalyst is regenerated in this manner depends upon the particular catalyst employed and the rate at which this catalyst is deactivated by contact with bis(fluoromethyl)ether, as well as the degree of deactivation which the operator is prepared to tolerate. Generally however, the catalyst may be contacted with an oxidising agent after from about a few hours, say about 2 to 4 hours, to about a few days, say about 4 or 5 days.

Preferably however, the catalyst is contacted with bis(fluoromethyl)ether and the oxidising agent simultaneously, that is the catalyst may be contacted with an oxidising agent whist bis(fluoromethyl)ether is contacted with the catalyst, since there is in this way no temporary loss of production. The oxidising agent may be periodically or continuously contacted with the catalyst whilst bis(fluoromethyl)ether is contacted with the catalyst.

The oxidising agent may comprise oxygen itself or a mixture comprising oxygen, for example air. Alternatively the oxidising agent may comprise a compound containing oxygen, for example nitrous oxide. Air is a particularly preferred oxidising agent.

Where the oxidising agent is contacted with the catalyst whilst bis(fluoromethyl)ether is also contacted with the catalyst, the conditions of temperature and pressure will usually be in the range at which the production of difluoromethane is carried out (as hereinbefore described). Hydrogen fluoride and/or a diluent may also be present. Where however, contact of the catalyst with an oxidising agent is carried out separately from difluoromethane production, the temperature at which the catalyst is contacted with the oxidising agent may be in the range from about 150° C. to about 450° C., and atmospheric, superatmospheric, for example up to about 10 bar or even higher, or subatmospheric pressures may be employed. Hydrogen fluoride and/or a diluent gas may also be present.

We have also found that certain catalysts are optimally treated by contact with an oxidising agent, and are therefore preferred catalysts for the process of the invention in which the catalyst preferably has, not only catalytic activity for the conversion of bis(fluoromethyl)ether to difluoromethane but also stability to, and promotion of, the oxidation of the deactivating carbonaceous layer upon the surface of the catalyst. Thus, we have found that preferred catalysts, in addition to having catalytic activity for the conversion of bis(fluoromethyl)ether to difluoromethane, also promote the oxidation of the deactivating carbonaceous layer on the catalyst surface. Preferred catalysts comprise an oxidation promoting metal, in particular copper, iron and chromium. Other oxidation promoting metals, for example variable valency transition metals such as cobalt, manganese, molybdenum, tungsten, rhenium, cerium and silver may also be employed. The oxidation promoting metal, for example copper, may be carried on a suitable support, for example one of the preferred catalysts employed for the conversion of bis(fluoromethyl)ether to difluoromethane, for example a metal oxide, fluoride or oxyfluoride, such as chromia, iron oxide, alumina and magnesia. Furthermore, the oxidation promoting metal may be present in the form of a compound thereof, for example copper chromite. The oxidation promoting metal may be present, in whatever form, as a mixture with other metals or compounds thereof. Indeed we have also found that certain combinations of metals, for example iron and chromium, copper and chromium, and zinc and chromium have both high stability under the catalyst treatment conditions and very high reaction selectivities for the conversion of bis(fluoromethyl)ether to difluoromethane. Particular preferred catalysts are those comprising iron and chromium, copper and chromium, or zinc and chromium, or mixtures of compounds thereof.

Where air is the oxidising agent contacted with the catalyst whilst bis(fluoromethyl)ether is also contacted with the catalyst, the proportion of oxidising agent to bis(fluoromethyl)ether which is employed may be in the molar range from about 2:1 to about 1:20, preferably in the range from about 1:1 to about 1:6.

The oxidising agent employed may, depending upon the amount employed, not be completely consumed during the process so that the oxidising agent may, if not removed, also be present in the off-gases from the reactor, together with the products of the reaction, difluoromethane, formaldehyde and hydrogen fluoride, and the products of the oxidation of the carbonaceous layer, carbon monoxide and carbon dioxide. We prefer however, in order to reduce the flammability hazard of this mixture that means are provided to consume any oxidising agent not consumed by contact with the catalyst. In particular we prefer that a catalyst bed (hereafter the second catalyst bed) is provided, subsequent to the main catalyst bed which functions to convert any unconsumed oxidising agent to carbon dioxide and water. The second catalyst bed may be provided in the same reactor as, but after the main catalyst bed, or it may be provided in a second reactor to which the off-gases from the first reactor are passed. The catalyst employed in the second catalyst bed may be any incineration catalyst, for example a catalyst comprising a noble metal, for example platinum or a catalyst comprising one of the oxidation promoting metals hereinbefore described.

After completion of the reaction, the difluoromethane may be isolated from unchanged starting materials and by-products using conventional procedures, for example distillation.

It is particularly convenient to operate the process of the invention as a continuous process wherein unchanged bis(fluoromethyl)ether and any hydrogen fluoride present in the difluoromethane product stream are recycled to the reaction zone.

Whilst processes are known for the production of at least some α-fluoroethers and in particular for the production of bis(fluoromethyl)ether, a particularly convenient and thus preferred general method for the production of the α-fluoroether is by reacting a non-enolisable aldehyde with hydrogen fluoride, preferably in the liquid phase, and reacting the resulting intermediate with an alcohol to form an α-fluoroether.

A non-enolisable aldehyde is required in order that the aldehyde is not polymerised in hydrogen fluoride when the two are reacted together.

According to a preferred embodiment of the invention there is provided a process for the production of a hydro(halo)fluorocarbon which comprises (a) reacting a non-enolisable aldehyde with hydrogen fluoride to form an intermediate and reacting the intermediate with an alcohol to produce an α-fluoroether and (b) contacting the α-fluoroether with a catalyst at elevated temperature and in the vapour phase wherein the catalyst is treated whereby to maintain and/or restore its activity.

The intermediate obtained by reacting the non-enolisable aldehyde with hydrogen fluoride may be reacted with the alcohol in a number of ways. The aldehyde and the hydrogen fluoride may be reacted in the presence of alcohol. Alternatively the aldehyde and the hydrogen fluoride may be reacted to form an equilibrium mixture containing the intermediate and the alcohol may be added to the equilibrium mixture. In a modification of this alternative, the intermediate may be separated from the equilibrium mixture before it is reacted with the alcohol.

It is to be understood that the intermediate derived from the non-enolisable aldehyde and hydrogen fluoride may itself be an α-fluoroether and that incomplete reaction of such an intermediate with the alcohol may therefore result in a mixture of α-fluoroethers.

The non-enolisable aldehyde is preferably formaldehyde or trifluoroacetaldehyde; formaldehyde is particularly preferred. In an embodiment both formaldehyde and trifluoroacetaldehyde are reacted with hydrogen fluoride to produce a mixture of $CF_3CFH-O-CH_2F$ and $CH_2F-O-CH_2F$. The mixture of aldehydes generates an alcohol in situ and the resulting α-fluoroether mixture may be converted to hydrofluoroalkanes. If desired, a separate alcohol may be added to the mixture to produce further α-fluoroethers.

The non-enolisable aldehyde may be provided in any of its known forms. Thus formaldehyde may be provided, for example, in one of its polymeric forms, paraformaldehyde or trioxane, or in its monomeric form which may be provided, for example, from a process stream in which it has been freshly made, for example by the oxidation of methanol. Trifluoroacetaldehyde may be provided, for example, in its hydrated form $CF_3CH(OH)_2$ or in its deydrated form $CF_3CHO$.

Accordingly, whenever used herein the term non-enolisable aldehyde is to be understood as including non-enolisable aldehydes, in any of their known forms.

In general, where formaldehyde is used as the non-enolisable aldehyde, a polymeric form of formaldehyde such as paraformaldehyde is preferred where the formaldehyde is dissolved in liquid hydrogen fluoride. Paraformaldehyde and trioxane dissolve readily in liquid hydrogen fluoride and the production of the intermediate for the α-fluoroether may be conveniently carried out by dissolving paraformaldehyde or trioxane in liquid hydrogen fluoride at about room temperature and at about atmospheric pressure.

The molar ratio of the non-enolisable aldehyde to hydrogen fluoride may vary considerably, for example in the range about 1:0.5 to 1:50 but in general a stoichiometric excess of hydrogen fluoride is preferred. Typically, the molar ratio of non-enolisable aldehyde to hydrogen fluoride will be in the range about 1:2 to about 1:10.

In one embodiment of the invention the non-enolisable aldehyde is reacted with hydrogen fluoride in the presence of an alcohol. In this case, the alcohol may be generated in situ. Thus, for example, reaction of the non-enolisable aldehyde trifluoroacetaldehyde with hydrogen fluoride is believed to yield an alcohol $CF_3CHFOH$ which may then condense to give the α-fluoroether $CF_3CFH-O-CFHCF_3$.

A wide range of α-fluoroethers may be produced by adding a separate alcohol. Where a separate alcohol is added, it may be added at the same time as the hydrogen fluoride and non-enolisable aldehyde, or it may be added subsequently to the mixture of aldehyde and hydrogen fluoride. Furthermore the alcohol may be first added to the hydrogen fluoride and the aldehyde may then be added to this reaction mixture. Thus the order of addition of the hydrogen fluoride, aldehyde and alcohol is not critical.

Where the alcohol is added separately, a primary alcohol is preferred which may have the general formula R-OH where R is as hereinbefore described. The alcohol must be inert to hydrogen fluoride and the α-fluoroether. The group R becomes the R group of the ether produced having the general formula $R-O-CFR_1R^2$, the groups $R^1$ and $R^2$ being as hereinbefore described.

The group R will usually be a straight chain alkyl or substituted alkyl group although it may also be a branched chain group. The R group may comprise only hydrogen and carbon, for example the R group may be $CH_3$ or $C_2H_5$. Preferably however, the R group will be fluorinated, for example the R group may be $FCH_2CH_2-$, $HCF_2CH_2-$, $CF_3CH_2-$, $(CF_3)_2CH-$, or $CF_2HCF_2CH_2$-. The alcohol R-OH is preferably a primary alcohol and may be, for example, methanol, ethanol, 2-monofluoroethanol, 2,2-difluoroethanol, 2,2,2-trifluoroethanol, hexafluoroisopropanol or 1,1,2,2-tetrafluoropropanol. Some at least of the alcohols may be generated in situ, for example by adding an epoxide to the non-enolisable aldehyde/hydrogen fluoride mixture. Thus for example, 2-monofluoroethanol may be generated in situ by the addition of ethylene glycol which reacts with hydrogen fluoride to produce 2-monofluoroethanol.

Where the alcohol is added separately, it may be added in similar proportions as the non-enolisable aldehyde, that is in the molar ratio of alcohol to hydrogen fluoride in the range about 1:0.5 to 1:50 but in general a stoichiometric excess of hydrogen fluoride is preferred. The optimum proportion of alcohol added may depend upon the particular alcohol used since we have found that with certain alcohols, the addition of too great a proportion of the alcohol leads to the formation of an undesirable acetal rather than the required α-fluoroether. Typically the molar ratio of alcohol to hydrogen fluoride will be in the range of from about 1:2 to about 1:10.

The α-fluoroether may be isolated from the mixture in which it is produced, and any by-products, before the α-fluoroether is heated to elevated temperature. The ether may be isolated, for example, by adding alkali to the mixture and heating the resulting alkaline solution, for example up to about 50° C., in order to drive off the α-fluoroether. Alternatively the α-fluoroether may conveniently be isolated by contacting the product stream with water at a temperature in the range from about 50° C. to about 80° C. The α-fluoroether may then be collected in a cold trap or passed directly to the heating zone.

The α-fluoroether may be introduced into the heating zone in undiluted form although it is generally convenient to introduce it in conjunction with a diluent such as an inert carrier gas, for example nitrogen.

In the embodiment of the invention wherein the α-fluoroether is generated by dissolving a non-enolisable aldehyde in liquid hydrogen fluoride and reacting the resulting intermediate with an alcohol, the α-fluoroether and the hydrogen fluoride in which it is dissolved may be vaporised together into the heating zone together with any unreacted aldehyde in the solution. In this case it may be a mixture of α-fluoroethers which is vaporised into the heating zone, so that a mixture of hydrofluoroalkanes are produced by heating the mixture of α-fluoroethers to elevated temperature. We especially prefer that the α-fluoroether and optionally hydrogen fluoride are separated from water which is also produced by the reaction of the non-enolisable aldehyde with hydrogen fluoride. Thus the α-fluoroether and optionally hydrogen fluoride are preferably passed to the heating zone in the substantial absence of water. Separation of the α-fluoroether and optionally hydrogen fluoride from water may be achieved in any suitable manner, conveniently for example by vaporising the α-fluoroether and optionally hydrogen fluoride from the product mixture or by contacting the product mixture with a solid drying agent. Thus for example a stream of an inert gas, for example nitrogen may be sparged through the product mixture.

Accordingly, in a further embodiment of the invention there is provided a process for the production of a hydrofluoroalkane which comprises the steps of (a) reacting a non-enolisable aldehyde with liquid hydrogen fluoride and reacting the resulting intermediate with an alcohol to produce an α-fluoroether, (b) separating at least some water from the product of step (a) and (c) contacting the α-fluoroether and hydrogen fluoride from step (b) in the vapour phase and at elevated temperature with a catalyst wherein the catalyst in step (c) is treated whereby to maintain and/or restore its activity.

Where the α-fluoroether is generated in the liquid phase, the non-enolisable aldehyde/hydrogen fluoride/alcohol liquid mixture is preferably held in the liquid phase in order to prevent any premature decomposition of the α-fluoroether such as may occur in the vapour phase. The temperature of the liquid mixture is therefore conveniently maintained below the boiling point of the product mixture, preferably at a temperature from about −10° C. to about 20° C.

The production of the especially preferred starting α-fluoroether, bis(fluoromethyl)ether is described in our published European Application No. 0 518 506, the contents of which, as stated previously, are incorporated herein by reference.

The invention is illustrated but not limited by the following examples.

EXAMPLE 1.

1 g of a catalyst of particle size 1 mm and comprising 6% copper on chromia (prepared by impregnating chromia with a solution of copper (II) chloride) was charged to a ¼" diameter Inconel vapour phase reactor tube and bis(fluoromethyl)ether, hydrogen fluoride and air were passed over the catalyst at 350° C. and atmospheric pressure and at flow rates of 1.5 mls/minute, 4.5 mls/minute and 0.45 mls/minute respectively, for 43 hours. After 21 hours the temperature was increased to 370° C. After 43 hours the air flow rate was increased to 0.9 mls/minute whilst maintaining the same bis(fluoromethyl)ether and hydrogen fluoride flow rates and the experiment was continued for a further 20 hours.

The off gases from the reactor were periodically sampled and analysed by gas chromatography in order to determine the amount of bis(fluoromethyl)ether present in the off-gas and hence monitor the conversion of bis(fluoromethyl)ether. The results are shown in Table 1.

TABLE 1

| TIME. (hours) | BFME Conversion. (%) |
|---|---|
| 0.2 | 99.6 |
| 1.4 | 99.8 |
| 16.7 | 88.5 |
| 21.0 | 54.8 |
| (TEMP −370° C.) | |
| 25.7 | 61.3 |
| 40.5 | 57.7 |
| 43.0 | 57.0 |
| (AIR FLOW DOUBLED) | |
| 44.0 | 68.0 |
| 46.5 | 100.0 |
| 49.0 | 86.0 |
| 64.1 | 99.85 |
| 97.1 | 96.2 |

EXAMPLE 2.

The procedure of example 1 was repeated except that the air flow was introduced after 6 hours operation with a constant rate of 0.9 mls/minute and the temperature was maintained constant at 350° C.

The off gases were analysed as described in example 1 except that some of the reactor off-gas samples were analysed to determine the composition of the volatile organics in the off gases. The results are shown in Table 2.

TABLE 2

| TIME. (hours) | BFME Conversion. (%) | Selectivity (%) | | | |
|---|---|---|---|---|---|
| | | $CH_2F_2$ | $CH_3F$ | $CH_4$ | Others |
| 0.5 | 98.9 | (NO ANALYSIS) | | | |
| 1.6 | 97.6 | (NO ANALYSIS) | | | |
| 4.9 | 84.7 | 94.2 | 1.9 | 0.26 | 3.67 |
| 6.0 | 63.4 | (NO ANALYSIS) | | | |
| (AIR FLOW INTRODUCED 0.9 mls/minute) | | | | | |
| 7.2 | 76.8 | (NO ANALYSIS) | | | |
| 21.1 | 96.7 | 95.4 | 3.6 | 0.2 | 0.8 |
| 24.6 | 94.0 | (NO ANALYSIS) | | | |
| 29.5 | 82.4 | 95.5 | 1.4 | 0.2 | 2.9 |
| 48.7 | 88.3 | (NO ANALYSIS) | | | |
| 73.8 | 96.1 | (NO ANALYSIS) | | | |
| (AIR TURNED OFF) | | | | | |
| 74.5 | 74.7 | (NO ANALYSIS) | | | |
| 75.7 | 54.3 | 97.9 | 1.0 | 0.3 | 0.8 |
| 76.9 | 42.1 | (NO ANALYSIS) | | | |

EXAMPLE 3.

The procedure of example 1 was repeated except that the catalyst comprised 1 g of chromia of particle size 1 mm which had been pre-fluorinated by heating in hydrogen fluoride at 300° C. for 16 hours and the air flow rate was 0.9 mls/minute. The temperature was maintained constant at 330° C. After 40 hours the air flow was turned off and after a further two hours the air flow was turned back on. The results are shown in Table 3.

TABLE 3

| TIME. (hours) | BFME Conversion. (%) | Selectivity (%) | | | |
|---|---|---|---|---|---|
| | | $CH_2F_2$ | $CH_3F$ | $CH_4$ | Other |
| 0.4 | 99.4 | 48.8 | 45.8 | 0.1 | 5.3 |
| 17.7 | 99.3 | 85.6 | 11.6 | 0.1 | 2.6 |
| 20.2 | 99.1 | 87.3 | 11.4 | 0.2 | 1.1 |
| 42.0 | 97.4 | 87.4 | 9.5 | 0.1 | 3.0 |
| (AIR FLOW OFF) | | | | | |
| 42.4 | 98.6 | 90.2 | 7.4 | 0.2 | 2.2 |
| 43.4 | 85.4 | 92.6 | 3.7 | 0.1 | 3.6 |
| 43.9 | 75.9 | 96.8 | 2.9 | 0.2 | 0.1 |
| (AIR FLOW ON) | | | | | |
| 44.5 | 94.4 | 93.5 | 5.6 | 0.2 | 0.7 |
| 66.6 | 96.9 | 91.2 | 8.2 | 0.2 | 0.4 |
| 84.2 | 97.7 | 88.6 | 8.0 | 0.2 | 3.2 |

EXAMPLE 4.

1 g of a catalyst of particle size 1 mm and comprising an intimate mixture of iron oxide and chromia in the molar ratio 9:1 was charged to a ¼" diameter Inconel vapour phase reactor tube and the catalyst was aged by passing bis(fluoromethyl)ether and hydrogen fluoride over the catalyst for 20 hours at atmospheric pressure and at flow rates of 1.5 mls/minute and 4.5 mls/minute and then passing bis(fluoromethyl)ether, hydrogen fluoride and air over the catalyst for a further 24 hours at flow rates of 1.5 mls/minute, 4.5 mls/minute and 0.45 mls/minute respectively, whilst steadily increasing the temperature to an operating temperature after 44 hours of 370° C.

The activity of this aged catalyst was then tested by continuing the bis(fluoromethyl)ether, hydrogen fluoride and air flows over the catalyst for a further 2 hours and then switching the air flow off, but continuing the bis(fluoromethyl)ether and hydrogen fluoride flows for a further 1 hour. The bis(fluoromethyl)ether and hydrogen fluoride flows over the catalyst were then switched off and the air flow over the catalyst was switched on for 30 minutes whilst the temperature was increased to 400° C. After this time the bis(fluoromethyl)ether and hydrogen fluoride flows over the catalyst were switched back on, whilst maintaining the air flow over the catalyst.

The off gases from the reactor were periodically sampled and analysed by gas chromatography in order to monitor the conversion of bis(fluoromethyl)ether and the composition of the volatile organics in the off gases. The results are shown in Table 4.

TABLE 4

| TIME. (hours) | BFME Conversion. (%) | Selectivity (%) | | | |
|---|---|---|---|---|---|
| | | $CH_2F_2$ | $CH_3F$ | $CH_4$ | Other |
| 44.0 | 59.6 | 95.2 | 3.4 | 0.5 | 0.9 |
| 46.0 | 57.8 | 95.3 | 13.5 | 0.6 | 0.6 |
| (AIR FLOW OFF) | | | | | |
| 46.3 | 61.1 | 90.4 | 5.2 | 0.9 | 3.5 |
| 46.6 | 47.3 | (NO ANALYSIS) | | | |
| 47.0 | 34.8 | (NO ANALYSIS) | | | |
| (AIR REGENERATION FOR 30 minutes at 400° C.) | | | | | |
| 48.8 | 97.8 | 97.1 | 2.2 | 0.2 | 0.5 |

EXAMPLE 5.

1 g of a catalyst of particle size 0.5–1.4 mm and comprising 6% copper on alumina (prepared by impregnating alumina with a solution of copper (II) chloride) was charged to a ¼" diameter Inconel vapour phase reactor tube and the catalyst was dried for 30 minutes under nitrogen (30 ml/minute) at 350° C. The nitrogen was then switched off and the catalyst was prefluorinated with hydrogen fluoride (4.5 ml/minute) for 16 hours.

Bis(fluoromethyl)ether, hydrogen fluoride and air were passed over the catalyst at 350° C. and atmospheric pressure and at flow rates of 1.5 mls/minute, 4.5 mls/minute and 0.9 mls/minute respectively, for 50 hours.

The off gases from the reactor were periodically sampled and analysed by gas chromatography. The results are shown in Table 5.

TABLE 5

| TIME. (hours) | BFME Conversion. (%) | Selectivity (%) | | | |
|---|---|---|---|---|---|
| | | $CH_2F_2$ | $CH_3F$ | $CH_4$ | Other |
| 0.7 | 100.0 | 83.2 | 9.8 | 0.9 | 6.0 |
| 3.2 | 100.0 | 86.4 | 12.3 | 0.3 | 1.0 |
| 6.8 | 98.7 | 87.6 | 10.7 | 0.3 | 1.4 |
| 22.9 | 99.9 | 86.1 | 11.8 | 0.3 | 1.8 |
| 28.7 | 95.9 | 94.8 | 4.2 | 0.2 | 0.8 |
| 46.8 | 100.0 | 94.5 | 4.9 | 0.2 | 0.4 |
| 51.1 | 95.8 | 94.5 | 4.6 | 0.2 | 0.7 |

EXAMPLE 6.

10 g of a catalyst of particle size 1.4–2 mm and comprising 16% copper(II)oxide on chromia (prepared by co-precipitating chromia and copper oxide from a solution of copper and chromium nitrates and then calcining in air) was charged to a ½" diameter Inconel vapour phase reactor tube and the catalyst was dried overnight under nitrogen (30 ml/minute) at 350° C. The nitrogen was then switched off and the catalyst was prefluorinated with hydrogen fluoride/air (4.5 ml/minute) for 16 hours.

Bis(fluoromethyl)ether, hydrogen fluoride, air and nitrogen were passed over the catalyst at 350° C. and 3 barg pressure and at flow rates of 15 mls/minute, 75 mls/minute, 9 mls/minute and 150 mls/minute respectively, for 140 hours.

The off gases from the reactor were periodically sampled and analysed by gas chromatography. The results are shown in Table 6.

TABLE 6

| TIME. (hours) | BFME Conversion. (%) | Selectivity (%) | | |
|---|---|---|---|---|
| | | $CH_2F_2$ | $CH_3F$ | Other |
| 1.4 | 96.8 | 74.6 | 22.1 | 3.2 |
| 3.9 | 94.3 | 79.8 | 14.4 | 5.8 |
| 20.2 | 99.3 | 69.6 | 29.7 | 0.7 |
| 25.7 | 96.3 | 69.3 | 6.9 | 3.8 |
| 52.0 | 92.3 | 77.3 | 14.9 | 7.8 |
| 72.1 | 98.7 | 78.5 | 20.1 | 1.3 |
| 93.8 | 88.3 | 77.8 | 10.5 | 11.7 |
| 120.7 | 98.7 | 84.2 | 14.5 | 1.3 |
| 142.4 | 98.4 | 91.5 | 6.9 | 1.6 |

EXAMPLE 7.

1 g of a catalyst of particle size 0.5–1.4 mm and comprising 8% zinc on chromia (prepared by co-precipitating zinc oxide and chromia from a solution of zinc and chromium nitrates and then calcining in air) was charged to a ¼" diameter Inconel vapour phase reactor tube and the catalyst was dried under nitrogen (30 ml/minute) for 2 hours at 300° C. after which time the nitrogen was turned off and hydrogen fluoride and air were passed over the catalyst at 300° C. and flow rates of 4.5 ml/minute and 0.9 ml/minute respectively for 16 hours. After this time and whilst maintaining the hydrogen fluoride and air feeds over the catalyst, the temperature was increased to 350° C. and bis(fluoromethyl)ether was passed over the catalyst with a flow rate of 1.5 ml/minute. After 5 hours the air feed was switched off. After a further 24 hours the air feed was switched on (0.9 ml/minute). After 1 hour the air was switched off. After a further 3 hours the air was switched on. After 17 hours the air was switched off. After 5 hours the bis(fluoromethyl)ether feed was switched off, and hydrogen fluoride and air were passed over the catalyst for 16 hours. After this time bis(fluoromethyl)ether, hydrogen fluoride and air were passed over the catalyst at 350° C.

The off Eases from the reactor were periodically sampled and analysed by gas chromatography. The results are shown in Table 7.

TABLE 7

| TIME. (hours) | BFME Conversion. (%) | Selectivity (%) | | | |
|---|---|---|---|---|---|
| | | $CH_2F_2$ | $CH_3F$ | $CH_4$ | Other |
| 0.1 | 96.9 | 56.6 | 42.6 | 0.2 | 0.6 |
| 3.0 | 96.7 | 65.4 | 31.7 | 0.2 | 2.7 |
| 4.4 | 97.3 | 71.2 | 25.9 | 0.3 | 2.7 |
| (AIR FLOW OFF) | | | | | |
| 6.1 | 98.7 | 82.8 | 15.9 | 0.2 | 1.2 |
| 9.8 | 90.4 | 90.9 | 8.5 | 0.1 | 0.5 |
| 12.8 | 95.6 | 94.0 | 5.7 | 0.1 | 0.1 |
| 30.2 | 58.8 | 98.2 | 1.3 | 0.3 | 0.2 |
| (AIR FLOW ON) | | | | | |
| 31.3 | 76.2 | 97.0 | 2.7 | 0.2 | 0.1 |
| (AIR FLOW OFF) | | | | | |
| 32.1 | 91.7 | 95.8 | 4.0 | 0.1 | 0.1 |
| 35.4 | 63.4 | 98.0 | 1.6 | 0.2 | 0.2 |
| (AIR FLOW ON) | | | | | |
| 37.1 | 94.6 | 95.9 | 4.0 | 0.1 | 0.0 |

TABLE 7-continued

| TIME. (hours) | BFME Conversion. (%) | Selectivity (%) | | | |
|---|---|---|---|---|---|
| | | $CH_2F_2$ | $CH_3F$ | $CH_4$ | Other |
| 57.4 | 94.4 | 94.3 | 5.5 | 0.1 | 0.1 |
| (AIR FLOW OFF) | | | | | |
| 64.2 | 84.7 | 96.6 | 3.2 | 0.1 | 0.1 |
| (BFME OFF: HF AND AIR ON FOR 16 HOURS) | | | | | |
| 80.6 | 94.4 | 69.6 | 30.0 | 0.3 | 0.1 |

EXAMPLE 8.

1 g of the pre-fluorinated catalyst as described in example 3 was charged to a ¼" diameter Inconel reactor tube and bis(fluoromethyl)ether and hydrogen fluoride were passed over the catalyst for 19 hours at 180° C., atmospheric pressure and flow rates of 2.0 mls/minute and 4.5 mls/minute respectively. After 19 hours the conversion of bis(fluoromethyl)ether had dropped from an initial conversion of >99% to about 2%.

After this time the bis(fluoromethyl)ether and hydrogen fluoride feeds were switched off and the temperature was increased to 300° C. whilst nitrogen was passed over the catalyst at 4.5 mls/minute for 360 minutes.

The nitrogen feed was switched off, the temperature returned to 180° C. and bis(fluoromethyl)ether and hydrogen fluoride were passed over the catalyst at the previous flow rates. The conversion of bis(fluoromethyl)ether was >15%.

EXAMPLE 9.

1 g of the catalyst as described in example 7 was dried under nitrogen (30 mls/minute) for 30 minutes at 350° C. and atmospheric pressure, and then hydrogen fluoride was passed over the catalyst for 16 hours at 350° C. After this time bis(fluoromethyl)ether and hydrogen fluoride were passed over the catalyst at 1.5 mls/minute and 4.5 mls/minute respectively at 200° C. The initial bis(fluoromethyl)ether conversion was 100% and difluoromethane selectivity was 85%. After 16 hours, the bis(fluoromethyl)ether conversion had fallen to 24%.

The bis(fluoromethyl)ether and hydrogen fluoride feeds were then switched off and the catalyst was heated at 300° C. under nitrogen (30 mls/minute) for 16 hours. After this time the bis(fluoromethyl)ether and hydrogen fluoride feeds were switched on again, the temperature was lowered to 200° C. The conversion had increased to 33% and the difluoromethane selectivity was 93%. After 24 hours the conversion had dropped to 18% and the difluoromethane selectivity was 94%.

We claim:

1. A process for the production of difluoromethane which comprises contacting bis(fluoromethyl) ether in the vapour phase at an elevated temperature with a catalyst which comprises (i) a metal selected from the group consisting of aluminum, chromium, copper, iron and nickel or an alloy or mixture of at least one of these metals, or (ii) an oxide, fluoride or oxyfluoride of at least one of the metals or alloys defined in (i) and wherein the catalyst is treated to maintain and/or restore its activity and wherein the catalyst treatment comprises either:

(i) heating the catalyst to an elevated temperature above about 250° C. in the absence of the bis(fluoromethyl) ether, or (ii) contacting the catalyst at an elevated temperature with an oxidising agent.

2. A process as claimed in claim 1 which comprises contacting the catalyst at an elevated temperature with an oxidising agent.

3. A process as claimed in claim 2 in which the catalyst is simultaneously contacted with the α-fluoroether and the oxidising agent.

4. A process as claimed in claim 3 in which the catalyst is continuously contacted with the oxidising agent.

5. A process as claimed in claim 2 in which the oxidising agent comprises oxygen.

6. A process as claimed in claim 5 in which the oxygen is passed over the catalyst in the form of air.

7. (Amended) A process as claimed in any one of claims 2 to 6 wherein the process is carried out in a reactor provided with means for consuming any oxidising agent not consumed by contact with the catalyst.